(12) United States Patent
Sevinc et al.

(10) Patent No.: US 10,174,175 B2
(45) Date of Patent: Jan. 8, 2019

(54) METHODS OF IMPROVING ADHESION OF NON-DI-(2-ETHYLHEXYL)PHTHALATE POLYVINYL CHLORIDE TO AN ACRYLIC- OR ABS-BASED POLYMER

(71) Applicants: Baxter International Inc., Deerfield, IL (US); Baxter Healthcare SA, Glattpark (Opfikon) (CH)

(72) Inventors: Zehra Sibel Sevinc, Round Lake, IL (US); Michael Tung Kiung Ling, Vernon Hills, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 160 days.

(21) Appl. No.: 15/173,936

(22) Filed: Jun. 6, 2016

(65) Prior Publication Data

US 2017/0349715 A1 Dec. 7, 2017

(51) Int. Cl.

| C08L 47/00 | (2006.01) |
| C08L 33/12 | (2006.01) |
| B32B 25/14 | (2006.01) |
| B32B 27/08 | (2006.01) |
| B32B 25/08 | (2006.01) |
| C08J 3/20 | (2006.01) |
| A61L 29/04 | (2006.01) |
| B32B 27/30 | (2006.01) |
| C08L 33/08 | (2006.01) |
| C08J 5/12 | (2006.01) |
| B29C 65/48 | (2006.01) |
| B29C 65/00 | (2006.01) |
| B29L 31/00 | (2006.01) |

(52) U.S. Cl.
CPC ............ *C08J 3/203* (2013.01); *A61L 29/041* (2013.01); *A61L 29/042* (2013.01); *A61L 29/049* (2013.01); *B32B 25/08* (2013.01); *B32B 25/14* (2013.01); *B32B 27/08* (2013.01); *B32B 27/304* (2013.01); *B32B 27/308* (2013.01); *C08J 5/122* (2013.01); *C08L 33/08* (2013.01); *C08L 33/12* (2013.01); *C08L 47/00* (2013.01); *B29C 65/4895* (2013.01); *B29C 66/71* (2013.01); *B29C 66/712* (2013.01); *B29L 2031/753* (2013.01); *B32B 2250/02* (2013.01); *B32B 2307/412* (2013.01); *B32B 2439/80* (2013.01); *B32B 2535/00* (2013.01); *C08J 2327/00* (2013.01); *C08J 2327/06* (2013.01); *C08J 2333/06* (2013.01); *C08J 2333/08* (2013.01); *C08J 2333/12* (2013.01); *C08J 2347/00* (2013.01); *C08J 2355/02* (2013.01); *C08J 2427/06* (2013.01); *C08J 2433/08* (2013.01); *C08J 2433/12* (2013.01); *C08J 2447/00* (2013.01); *C08L 2201/10* (2013.01); *C08L 2203/02* (2013.01); *C08L 2203/30* (2013.01); *C08L 2205/025* (2013.01); *C08L 2205/03* (2013.01); *C08L 2205/08* (2013.01)

(58) Field of Classification Search
None
See application file for complete search history.

(56) References Cited

U.S. PATENT DOCUMENTS

| 3,873,640 A * | 3/1975 | Owston ............... C08G 18/672 525/126 |
| 3,985,704 A | 10/1976 | Jones et al. |
| 4,098,719 A | 7/1978 | Hushebeck |
| 4,308,354 A | 12/1981 | Jung et al. |
| 4,556,589 A * | 12/1985 | Neumann ............... B32B 27/30 428/36.6 |
| 5,290,860 A | 3/1994 | Zimmerman et al. |
| 5,416,142 A | 5/1995 | Bush et al. |
| 6,822,045 B2 | 11/2004 | Miyatake et al. |
| 2006/0252865 A1 | 11/2006 | Bush et al. |
| 2014/0017335 A1† | 1/2014 | Dimov |

FOREIGN PATENT DOCUMENTS

| EP | 0985692 | 3/2000 |
| EP | 3012283 A1 | 4/2016 |
| WO | WO2005089832 A2 | 9/2005 |

OTHER PUBLICATIONS

Written Opinion of the International Preliminary Examining Authority issued in related International Patent Application No. PCT/US2017/033588 dated May 7, 2018.
International Preliminary Report on Patentability issued in related International Patent Application No. PCT/US2017/033588 dated Aug. 17, 2018.
Cyro Tech Brief, Applications, Solvent & Adhesive Bonding, Cyro Industries, 1999, pp. 1-4.†
Evonik Industries, Acrylic Advisor, Technical reference guide for CYROLITE, XT polymer, CYREX, Vu-Stat acrylic polymers, 2016, Evonik Cyro LLC, pp. 1-42.†
Evonik Industries, Polymer Solutions for the Medical Device Industry, 2015, Evonik Cyro LLC, pp. 1-24.†

(Continued)

*Primary Examiner* — Sheeba Ahmed
(74) *Attorney, Agent, or Firm* — K&L Gates LLP

(57) ABSTRACT

The present disclosure provides methods of improving adhesion of a non-di-(2-ethylhexyl)phthalate (DEHP) plasticized polyvinyl chloride (PVC) to an acrylic-based polymer or an ABS-based polymer. Such methods may comprise blending the acrylic-based polymer or ABS-based polymer with an impact modifier so that a rubber content in the acrylic-based polymer or ABS-based polymer is greater than 12% (w/w). Also provided are components of a device (e.g., a medical device) made by the disclosed methods.

21 Claims, 1 Drawing Sheet

(56) References Cited

OTHER PUBLICATIONS

Evonik Industries, Molding compounds product portfolio, ACRYLITE, ACRYMID, CYROLITE, XT polymer, CYREX, 2012, Evonik Cyro LLC, pp. 1-28.†
Kucklick, The Medical Device R&D Handbook, 2nd Ed., Section 1, CRC Press, New York, 2013, pp. 19, 21.†
Evonik Industries, CYROLITE, ACRYLITE, and XT polymers, The world's most advanced medical acrylics, 2009, Evonik Cyro LLC, pp. 1-12.†

\* cited by examiner
† cited by third party

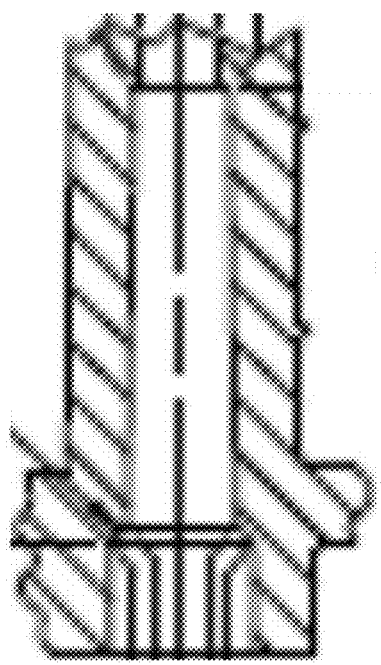

METHODS OF IMPROVING ADHESION OF NON-DI-(2-ETHYLHEXYL)PHTHALATE POLYVINYL CHLORIDE TO AN ACRYLIC- OR ABS-BASED POLYMER

BACKGROUND

Polyvinyl chloride (PVC) is one of the most prevalently used polymers in medical applications such as IV and blood bags, surgical tubing and related components, catheters, etc. Alone, PVC is a hard and rigid substance. However, when PVC is plasticized with a plasticizer, PVC becomes flexible yet strong, kink resistant, and can be easily solvent welded to other polymeric components using solvents such as cyclohexanone. However, the use of PVC has been hindered to some degree by the decay over time in the strength of its bond to other polymers such as an acrylic- or ABS-based polymer.

SUMMARY

The present disclosure provides methods of improving adhesion of non-di-(2-ethylhexyl)phthalate (DEHP) plasticized polyvinyl chloride (PVC) including, non-DEHP PVC based-polymer blends and articles or devices comprising such polymers and blends, to an acrylic-based polymer or an ABS-based polymer including, articles or devices comprising such polymers.

The methods of the present disclosure may comprise blending the acrylic-based polymer or ABS-based polymer with an impact modifier so that a rubber content in the acrylic-based polymer or ABS-based polymer is greater than 12% (w/w).

In some embodiments of each or any of the above- or below-mentioned embodiments, the non-DEHP plasticized PVC is di-2-ethylhexyl terephthalate (DEHT) plasticized PVC.

In some embodiments of each or any of the above- or below-mentioned embodiments, the non-DEHP plasticized PVC includes a plasticizer comprising non-DEHP plasticizer in an amount ranging from 15% (w/w) to 46% (w/w) based on the total weight of the plasticizer.

In some embodiments of each or any of the above- or below-mentioned embodiments, the non-DEHP plasticized PVC includes a plasticizer comprising non-DEHP plasticizer in an amount ranging from 6% (w/w) to 42% (w/w), excluding epoxidized oils.

In some embodiments of each or any of the above- or below-mentioned embodiments, the acrylic-based polymer is an impact modified, acrylic-based multipolymer.

In some embodiments of each or any of the above- or below-mentioned embodiments, the ABS-based polymer is an impact modified, ABS-based multipolymer.

In some embodiments of each or any of the above- or below-mentioned embodiments, the acrylic-based polymer is an acrylic terpolymer.

In some embodiments of each or any of the above- or below-mentioned embodiments, the acrylic terpolymer is a methyl methacrylate/styrene/ethyl acrylate terpolymer.

In some embodiments of each or any of the above- or below-mentioned embodiments, the ABS-based polymer is selected from the group consisting of (1) a methacrylate polymer containing ABS, (2) a transparent grade of ABS, and (3) methyl methacrylate-acrylonitrile-butadiene-styrene (MABS).

In some embodiments of each or any of the above- or below-mentioned embodiments, the acrylic-based polymer has a poly (methyl methacrylate) content greater than 98% (w/w).

In some embodiments of each or any of the above- or below-mentioned embodiments, the acrylic-based polymer is transparent.

In some embodiments of each or any of the above- or below-mentioned embodiments, the impact modifier is selected from the group consisting of: poly (butyl acrylate), poly (butyl methacrylate), polybutadiene, methylmethacrylate-butadiene-styrene copolymer (MBS), acrylic rubber, and Elvaloy®AC.

In some embodiments of each or any of the above- or below-mentioned embodiments, the acrylic-based polymer or the ABS-based polymer is blended with a polybutadiene-type impact modifier.

In some embodiments of each or any of the above- or below-mentioned embodiments, the acrylic-based polymer is blended with a polybutadiene-type impact modifier and/or poly (butyl acrylate) impact modifier.

In some embodiments of each or any of the above- or below-mentioned embodiments, the rubber content in the acrylic-based polymer or ABS-based polymer is greater than 12% (w/w) and up to 40% (w/w).

In some embodiments of each or any of the above- or below-mentioned embodiments, the rubber content in the acrylic-based polymer or ABS-based polymer is at least 15% (w/w).

The present disclosure also provides methods of bonding a first member comprising a non-DEHP plasticized PVC polymer, including a non-DEHP plasticized PVC polymer blend, to a second member comprising an acrylic-based polymer or an ABS-based polymer, the method comprising: blending the acrylic-based polymer or the ABS-based polymer with an impact modifier so that a rubber content in the acrylic-based polymer or ABS-based polymer is greater than 12% (w/w); forming the second member comprising the acrylic-based polymer or the ABS-based polymer; and solvent bonding the first member to the second member.

In some embodiments of each or any of the above- or below-mentioned embodiments, the non-DEHP plasticized PVC based-polymer (e.g., a non-DEHP PVC polymer blend) and acrylic-based polymer have a bond force greater than 5.5 lbf for at least 5 years.

In some embodiments of each or any of the above- or below-mentioned embodiments, the acrylic-based polymer or the ABS-based polymer is blended with a polybutadiene-type impact modifier.

In some embodiments of each or any of the above- or below-mentioned embodiments, the acrylic-based polymer is blended with a polybutadiene-type impact modifier and/or poly(butyl acrylate) impact modifier.

In some embodiments of each or any of the above- or below-mentioned embodiments, the first member is a tube and the second member is a molded part.

In some embodiments of each or any of the above- or below-mentioned embodiments, the first member and the second member are solvent bonded using cyclohexanone or a mixture of cyclohexanone and methyl ethyl ketone (MEK).

The present disclosure also provides a component of a device produced by a method comprising: blending the acrylic-based polymer or the ABS-based polymer with an impact modifier so that a rubber content in the acrylic-based polymer or ABS-based polymer is greater than 12% (w/w); forming the second member comprising the acrylic-based polymer or the ABS-based polymer; and solvent bonding the first member to the second member.

The present disclosure also provides a component of a device, the component comprising a first member that comprises non-DEHP PVC; and a second member that comprises an acrylic-based polymer or an ABS-based polymer molded part, wherein the first member is solvent bonded to the second member, and wherein the acrylic-based polymer or ABS-based polymer comprises an impact modifier so that a rubber content in the acrylic-based polymer or ABS-based polymer is greater than 12% (w/w).

BRIEF DESCRIPTION OF THE FIGURE

The foregoing summary, as well as the following detailed description of the disclosure, will be better understood when read in conjunction with the appended FIGURE. For the purpose of illustrating the disclosure, shown in the FIGURE is an embodiment that is presently preferred. It should be understood, however, that the disclosure is not limited to the precise arrangements, examples and instrumentalities shown.

FIG. 1 shows a cross sectional view of a molded part having a pocket for solvent bonding a tubing according to an embodiment of the present disclosure.

DETAILED DESCRIPTION

The present disclosure provides methods of improving adhesion of a non-di-(2-ethylhexyl)phthalate (DEHP) polyvinyl chloride (PVC) (e.g., a non-DEHP PVC polymer blend) to an acrylic-based polymer or an ABS-based polymer. In medical applications, a PVC containing article is often solvent bonded to an article comprising an acrylic-based polymer or an ABS-based polymer. In such applications, DEHP-free PVC compositions (e.g., a non-DEHP PVC polymer blend) are advantageous in view of growing concerns over leaching of DEHP from PVC articles. However, such bonds decay over time and as a result medical devices or components that include such bonds do not have suitable shelf-lives. Surprisingly, it was discovered that the adhesion (e.g., bond strength and/or bond life) of a non-di-(2-ethylhexyl)phthalate (DEHP) polyvinyl chloride (PVC) (e.g., a non-DEHP PVC polymer blend) to an acrylic-based polymer or an ABS-based polymer could be improved by blending the acrylic-based polymer or ABS-based polymer with an impact modifier and/or using a high molecular weight acrylic-based polymer or ABS-based polymer. The methods can be used to manufacture a medical device or a component of a medical device where the medical device or component includes an article comprising non-DEHP PVC bonded (e.g., a non-DEHP PVC polymer blend) to an article comprising an acrylic-based polymer or an ABS-based polymer.

Disclosed herein are methods of improving adhesion of a non-di-(2-ethylhexyl)phthalate (DEHP) polyvinyl chloride (PVC) to an acrylic-based polymer or an ABS-based polymer, the method comprising blending the acrylic-based polymer or ABS-based polymer with an impact modifier and/or using a high molecular weight acrylic-based polymer or ABS-based polymer. As used herein, the term "improving adhesion" means increasing, enhancing, or maintaining the strength of a joint (e.g., without significant deterioration of bond pull force (e.g., 3.5 lbf, 4.0 lbf, 4.5 lbf, 5.0 lbf, 5.5 lbf, 6.0 lbf, 6.5 lbf, 7.0 lbf, 7.5 lbf, 8.0 lbf, 8.5 lbf, 9.0 lbf, 9.5 lbf, 10.0 lbf or more) and/or the lifespan of a bond (e.g., reducing or maintaining bond decay) including, for example, over a period of years (e.g., 1, 2, 3, 4, 5, 6, 7, 8, 9, 10 or more years). Preferably, the bond maintains a pull force of at least 5.5 lbf for at least 5 years.

Non-DEHP plasticized PVC compound or blend suitable for use in the disclosure include medical-grade and food-grade polyvinyl chloride homopolymers. The PVC resin can be included in a composition or an article in any suitable amount, for example an amount in a range of about 35% (w/w) to about 90% (w/w). The preferred weight ratio of the amount of the PVC resin as compared to the combined amount of all additives can be any suitable ratio, for example a ratio in a range of about 0.5 to about 5, or about 1 to 3, or about 1 to 2.

The K value of PVC is correlated with the molecular weight of PVC and is often used as a proxy for molecular weight. PVC resins for use in the compositions described herein can be characterized by any suitable K value for the desired PVC article end use as is already known in the art, optionally a K value in a range of about 35 to about 80, optionally in a range of about 60 to about 80, for example 70.

The non-DEHP plasticized PVC polymer, including polymer blends, according to the disclosure can include other optional additive ingredients including, but not limited to, plasticizers, lubricants, impact modifiers, biocides, fillers, colorants, antioxidants, and other functional ingredients, for example in amounts suitable for their intended purpose.

The non-DEHP plasticized PVC polymer (e.g., a non-DEHP PVC polymer blend) according to the disclosure can include a primary and, optionally, a secondary plasticizer. Plasticizers for use in PVC compositions are well known in the art. Suitable plasticizers for use as a primary or secondary plasticizer include phthalate plasticizers, for example di-2-ethylhexylphthalate (DEHP), di(2-ethylhexyl) terephthalate (DEHT), di-butylphthalate (DBP), di-isobutylphthalate (DIBP), butyl benzylphthalate (BBP), and di(isononyl)phthalate (DINP), epoxidized vegetable oils, for example, soy and linseed, trimellitates, for example, trimethyl trimellitate (TMTM), tris(2-ethylhexyl)trimellitate (TOTM), and n-octyltrimellitate (OTM), polyesters, phosphates, for example, isodectyl diphenyl phosphate (DDP) and tris(2-ethylhexyl) phosphate (TOF), citrates, for example, butyryl trihexyl citrate (BTHC) and acetyl tributyl citrate (ATBC), benzoates, for example dipropylene glycol dibenzoate (DPGDP), sulphonates, for example, phenyl cresyl esters of pentadecyl sulfonic acid, carboxylates, cyclohexane based, such as di(isononyl)cyclohexane-1,2-dicarboxylate, castor oil derivatives, and adipates, for example, di-2-ethylhexyladipate (DEHA), dimethyladipate (DMAD), and dioctyladipate (DOA).

The primary plasticizers can be included in the non-DEHP PVC compositions in any suitable amount, for example in a range of about 30 phr to about 70 phr, or from about 35 phr to about 65 phr, or from about 30 phr to about 60 phr, or from about 25 phr to about 55 phr. In some embodiments, the PVC compositions will include a secondary plasticizer. A secondary plasticizer can be included in the PVC composition in any suitable amount, for example, up to about 30 phr. As less plasticizer is used, the PVC articles can become more brittle, whereas as more plasticizer is used the PVC articles can lose strength.

Lubricants for use in the non-DEHP plasticized PVC compositions according to the disclosure are well known in the art. Suitable lubricants include, but are not limited to, polyethylene, paraffin wax, and acrawax, for example N,N' ethylene bisstearamide. Lubricants can be included in the PVC compositions in an amount up to about 0.5 phr. In an embodiment, the non-DEHP plasticized PVC compositions according to the disclosure may not require any processing aid such as a lubricant.

The non-DEHP PVC compositions described herein can be formed into PVC articles. PVC articles can be made using any suitable equipment and method, including the various methods already commonly known in the art. The PVC articles can be heat-processed. For example, the PVC article can be made with one or more processing steps including, but not limited to, extrusion, extrusion blow molding, injection molding, injection blow molding, insert molding, rotational molding, thermoforming, vacuum forming, pultrusion, resin transfer molding, and welding.

The non-DEHP plasticized PVC based polymer may be a blend of two or more polymers and may be capable of being fabricated into a tubing (e.g., a tubing for use in a medical application) including, for example, a multiple layered tubing, or a dual lumen tubing. The tubing may have one or more of the following physical properties: a modulus of elasticity of less than about 20,000 psi, more preferably less than about 10,000 and most preferably less than about 5,000 psi, an internal haze of less than about 25% when measured in accordance with ASTM D1003, is capable of being fabricated at a throughput rate of greater than about 100 ft/min, more preferably greater than about 200 ft/min, even more preferably greater than about 250 ft/min and most preferably equal to or greater than about 300 ft/min; a yield strength of from about 400 psi to about 1500 psi and more preferably from about 600 psi to about 800 psi, and the tensile curve around the yield curve should be smooth, is capable of being repeatedly used with a medical tubing clamp with an occlusion force typically of about 5 lbs without significantly damaging the tubing and is capable of solvent bonding to a rigid component. In an embodiment, the tubing may be exposed to radiation.

The non-DEHP PVC based polymer may fabricated into tubing using standard polymer processing techniques such as extrusion, coextrusion, blow extrusion, blow molding, injection molding and the like. Similarly the blends can be fabricated into films or sheetings using standard polymer processing techniques such as extrusion, coextrusion, blow extrusion, blow molding, compression molding injection molding, lamination, thermoforming, calendaring and the like.

For tubings that are to be used with infusion pumps, especially those pumps that apply energy to a sidewall of the tubing, it is desirable the tubing is capable of delivering fluid in response to energy applied to the tubing by a medical infusion pump for a 24 hour period without more than 10% change in flow rate and more preferably without more than 5% change. It is also desirable for pump compatible tubing to have an original cross-sectional diameter and to retain 95% of the original cross-sectional diameter after stretching the tubing with a 5 lb weight for 10 seconds.

The non-DEHP plasticized PVC based polymer may be blended with one or more additives to make a tubing material. For example, the non-DEHP based polymer may comprise a blending resin of a polyolefin and more particularly homopolymers and copolymers of alpha-olefins. These additives may be blended into the tubing material in an amount from 5% to about 95% by weight of the tubing material. The alpha-olefins may contain from 2 to about 20 carbon atoms or any range or combination of ranges therein. Alpha-olefins containing from 2 to about 10 carbon atoms are more preferred. Thus, the olefin polymers may be derived from olefins such as ethylene, propylene, 1-butene, 1-pentene, 4-methyl-1-pentene, 1-octene, 1-decene, 4-ethyl-1-hexene, etc., or mixtures of two or more of these olefins. Examples of particularly useful olefin polymers include ethylene-butene copolymers and ethylene and propylene copolymers and ethylene and octene-1 copolymers which will be referred to as ultra-low density polyethylenes (ULDPE). Such ULDPE's have a density of preferably equal to or below 0.910 g/cm$^3$ and preferably are produced using metallocene catalyst systems. Such catalysts are said to be "single site" catalysts because they have a single, sterically and electronically equivalent catalyst position as opposed to the Ziegler-Natta type catalysts which are known to have multiple catalysts sites.

In some embodiments, a radiation sensitive additive may be added to the tubing material that is responsive to exposure to radiation such as gamma rays, electron beam, ultra-violet light, visible light or other ionizing energy sources. Suitable radiation sensitive additives include organic peroxides such as dicumyl peroxide (DiCup) and other free radical generating compounds. Other free-radical sensitive functional groups include acrylate, acid, dienes and their copolymers and terpolymers, amide, amine, silane, urethane, hydroyxl, epoxy, ester, pyrolidone, acetate, carbon monoxide, ketone, imidazoline, photo and UV initiators, fluoro-compounds, etc. These functional groups may be in polymeric and non-polymeric compounds. More particularly suitable additives include ethylene vinyl acetate, ethylene methyl acrylate (EMA), ethylene acrylic acid (EAA), fatty amides, low viscosity functionalized and non-functionalized styrene-butadiene copolymers and their hydrogenated derivatives, functionalized and non-functionalized polybutadiene, polyisoprene, ethylene propylene diene monomer terpolymer, polybutene, urethane acrylate, epoxy acrylate, photoinitiators, etc. The ethylene-propylene terpolymers have a third component of a chain nonconjugated diolefin e.g. 1,4-pentadiene, 1,4-hexadiene, 1,5-hexadiene or a cyclic polyene e.g., dicyclopentadiene, methylenenorbornene, ethylidenenorbornene, cyclooctadiene, methyltetrahydroindene, etc.

The radiation sensitive additives should be added to the tubing material in effective amounts preferably in an amount by weight of the monolayer or outer layer from 0.01-20.0%, more preferably from 0.01-10.0% and most preferably 0.02-5.0%.

Optionally, the tubing material may be further modified by incorporating polar additives to enhance their compatibility with adhesives such as cyanoacrylate type adhesives and improve other surface characteristics such as friction (lubrication). The polar additives preferably are selected from a non-polymeric aliphatic or aromatic hydrocarbon having greater than 5 carbon atoms but less than 500, more preferably less than 200 carbons and most preferably less than 100 carbons in the backbone. Further, the additives should have electron negative groups selected from the group of amines; amides; hydroxyls; acids; acetate, ammonium salts; organometallic compounds such as metal alcoholates, metal carboxylates, and metal complexes of numerous 1,3 dicarbonyl compounds; phenyl phosphines; pyridines; pyrrolidones; imidazoline, and oxazolines. The modification additive can also be a polymer emulsion or solution.

The polar additives should be included in an amount by weight of the tubing material from about 0.001%-10.00%, more preferably 0.01-2.0%.

The tubings may have an inner diameter dimension within the range of 0.003-0.4 inches, and an outer diameter dimension within the range of 0.12-0.50 inches. The tubing should be flexible having a modulus of elasticity of less than 50,000 psi, more preferably less than 30,000, even more preferably less than 10,000 and most preferably less than 4,000 psi, or any range or combination of ranges therein.

The adhesion of a non-DEHP PVC to an acrylic-based polymer or an ABS-based polymer may be improved by blending the acrylic-based polymer or ABS-based polymer with an impact modifier and/or increasing the molecular weight of the acrylic-based polymer or ABS-based polymer.

Impact modifiers that may be blended with an acrylic based polymer or an ABS-based polymer may include, for example, one or more impact modifiers selected from the group consisting of: poly(butyl acrylate), poly(butyl methacrylate), polybutadiene, methylmethacrylate-butadiene-styrene copolymer (MBS), acrylic rubber, or Elvaloy®AC. In another embodiment, an acrylic-based polymer or the ABS-based polymer may be blended with a polybutadiene-type impact modifier including, for example greater than 12% (w/w) and up to 40% (w/w) of the impact modifier. In yet another embodiment, an acrylic-based polymer may be blended with a polybutadiene-type impact modifier and/or poly(butyl acrylate) impact modifier including, for example, greater than 12 and up to 40% (w/w) of the impact modifier.

The acrylic-based polymer or the ABS-based polymer blended with impact modifier preferably has a rubber content greater than 12% (w/w), for example at least 15% (w/w). Depending on the usage requirements or preferences for the particular application, a rubber content in the acrylic-based polymer or ABS-based polymer of less than 12% (w/w) may not provide the requisite adhesion strength.

Articles comprising a non-DEHP PVC based polymer may be solvent bonded to another article including, for example, an acrylic- or ABS-based polymer as disclosed herein. Suitable polymers for fabricating component may additionally include homopolymers and copolymers of polypropylenes, polyesters, polyamides, polycarbonates, cyclic olefin containing polymers and bridged polycyclic olefin containing polymers. Suitable cyclic olefin containing polymers and bridged polycyclic olefin containing polymers.

Referring to FIG. 1, an article comprising an acrylic- or ABS-based polymer according to the present disclosure may be a rigid article such as a connector or other device commonly used in peritoneal dialysis or I.V. administration sets. The article may have a modulus of elasticity of greater than about 30,000 psi.

A solvent bonding technique may be used to join together any combination of rigid, semi-rigid and flexible parts including joining two rigid components, a rigid component to a semi-rigid component, a rigid component to a flexible component, a semi-rigid component to a flexible component, a semi-rigid component to another semi-rigid component, and certain flexible components to one another. Solvent bonding refers to exposure of one of the articles made from one of the polymers to a solvent to melt, dissolve or swell the product and then can be attached to another polymeric component to form a permanent bond. For example, an article comprising a non-DEHP PVC based polymer may be exposed to a solvent to bond it to a rigid article such as an article comprising an acrylic- or ABS-based polymer.

Suitable solvents typically include those having a solubility parameter of less than about 20 (MPa)$^{1/2}$, more preferably less than about 19 (MPa)$^{1/2}$ and most preferably less than about 18 (MPa)$^{1/2}$ and include, but are not limited to, aliphatic hydrocarbons, aromatic hydrocarbons, mixtures of aliphatic hydrocarbons, mixtures of aromatic hydrocarbons and mixtures of aromatic and aliphatic hydrocarbons. Suitable aliphatic hydrocarbons include substituted and unsubstituted hexane, heptane, cyclohexane, cycloheptane, decalin, and the like. Suitable aromatic hydrocarbons include substituted and unsubstituted aromatic hydrocarbon solvents such as xylene, tetralin, toluene, and cumene. Suitable hydrocarbon substituents include aliphatic substituents having from 1-12 carbons and include propyl, ethyl, butyl, hexyl, tertiary butyl, isobutyl and combinations of the same. Suitable solvents will also have a molecular weight less than about 200 g/mole, more preferably less than about 180 g/mole and most preferably less than about 140 g/mole.

The present disclosure further provides solvent bonded components such as components of a device used for peritoneal dialysis, hemodialysis, or hemodiafiltration. The components may be solvent bonded together by providing an article comprising a non-DEHP PVC based polymer, providing an article comprising an acrylic-based polymer or an ABS-based polymer, applying a solvent to one of the first article or the second article to define an interface area; and bonding the first article to the second article along the interface area.

The first article can be a rigid, semi-rigid and flexible medical product selected from the group consisting of Y-sites, filter housings, drip chambers, heparin locks, injection sites, catheters, spikes, syringe barrels, closures, tubings, oxygenators, pump cassettes, valves, burretes, and any medical article or component. The second article can be a rigid, semi-rigid and flexible polymeric material selected from the group comprising an acrylic-based polymer or an ABS-based polymer. The second article can be part of the same device set forth for the first article.

It may also be desirable to improve solvent bonding to provide a tubing having a textured, frosted or otherwise roughened outer surface in the area where the tubing will be bonded (the interface area) or along the entirety of the tubing outer surface.

The present disclosure also provides methods of bonding a first member comprising non-DEHP plasticized PVC to a second member comprising an acrylic-based polymer or an ABS-based polymer. The methods may comprise blending the acrylic-based polymer or the ABS-based polymer with an impact modifier or increasing the molecular weight of the acrylic-based polymer or ABS-based polymer; forming the second member comprising an acrylic-based polymer or an ABS-based polymer; and solvent bonding the first member to the second member. Alternatively, the methods may comprise bonding a first member comprising non-DEHP PVC to a second member comprising an acrylic-based polymer having an impact modifier or an ABS-based polymer having an impact modifier, the method comprising: providing a first member comprising non-DEHP PVC and a second member comprising an acrylic-based polymer having an impact modifier or an ABS-based polymer having an impact modifier; and solvent bonding the first member to the second member. Also provided is a component of a device (e.g., a device used for peritoneal dialysis, hemodialysis, or hemodiafiltration), the component comprising a first member bonded to a second member according to the methods disclosed herein.

As used herein and unless specified otherwise, the terms "wt. %" and "wt %" are intended to refer to the composition of the identified element in "dry" (non water) parts by weight of the entire composition (when applicable).

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Unless otherwise indicated, all numbers expressing quantities of ingredients, properties such as molecular weight, reaction conditions, and so forth used in the specification and claims are to be understood as being modified in all instances by the term "about."

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention is claimed as follows:

1. A method of improving adhesion of a non-di-(2-ethylhexyl)phthalate (DEHP) plasticized polyvinyl chloride (PVC) to an acrylic-based polymer or an ABS-based polymer, the method comprising:

blending the acrylic-based polymer or ABS-based polymer with an impact modifier so that a rubber content in the acrylic-based polymer or ABS-based polymer is greater than 12% (w/w), wherein the impact modifier is selected from at least one of poly(butyl acrylate), poly(butyl methacrylate), methyl methacrylate-butadiene-styrene copolymer (MBS), acrylic rubber, and Elvaloy®AC.

2. The method of claim 1, wherein the non-DEHP PVC is dioctyl terephthalate (DEHT) PVC.

3. The method of claim 1, wherein the non-DEHP plasticized PVC includes a plasticizer comprising non-DEHP plasticizer in an amount ranging from 15% (w/w) to 46% (w/w) based on the total weight of the plasticizer.

4. The method of claim 1, wherein the non-DEHP plasticized PVC includes a plasticizer comprising non-DEHP plasticizer in an amount ranging from 6% (w/w) to 42% (w/w), excluding epoxidized oils.

5. The method of claim 1, wherein the acrylic-based polymer is an impact modified, acrylic-based multipolymer.

6. The method of claim 1, wherein the ABS-based polymer is an impact modified, ABS-based multipolymer.

7. The method of claim 1, wherein the acrylic-based polymer is an acrylic terpolymer.

8. The method of claim 7, wherein the acrylic terpolymer is a methyl methacrylate/styrene/ethyl acrylate terpolymer.

9. The method of claim 1, wherein the ABS-based polymer is selected from the group consisting of (1) a methacrylate polymer containing ABS, (2) a transparent grade of ABS, and (3) methyl methacrylate-acrylonitrile-butadiene-styrene (MABS).

10. The method of claim 1, wherein the acrylic-based polymer has a poly (methyl methacrylate) content greater than 98% (w/w).

11. The method of claim 1, wherein the acrylic-based polymer is transparent.

12. The method of claim 1, wherein the acrylic-based polymer is blended with a poly(butyl acrylate) impact modifier.

13. The method of claim 1, wherein the rubber content in the acrylic-based polymer or ABS-based polymer is greater than 12% (w/w) and up to 40% (w/w).

14. A method of bonding a first member comprising non-DEHP PVC to a second member comprising an acrylic-based polymer or an ABS-based polymer, the method comprising:

blending the acrylic-based polymer or the ABS-based polymer with an impact modifier so that a rubber content in the acrylic-based polymer or ABS-based polymer is greater than 12% (w/w), wherein the impact modifier is selected from the at least one of poly(butyl acrylate), poly(butyl methacrylate), methyl methacrylate-butadiene-styrene copolymer (MBS), acrylic rubber, and Elvaloy®AC;

forming the second member comprising the acrylic-based polymer or the ABS-based polymer; and solvent bonding the first member to the second member.

15. The method of claim 14, wherein the non-DEHP PVC and acrylic-based polymer have a bond force greater than 5.5 lbf for at least 5 years.

16. The method of claim 14, wherein the acrylic-based polymer or the ABS-based polymer is blended with a polybutadiene-type impact modifier.

17. The method of claim 14, wherein the acrylic-based polymer is blended with a polybutadiene-type impact modifier and/or poly(butyl acrylate) impact modifier.

18. The method of claim 14, wherein the first member is a tube and the second member is a molded part.

19. The method of claim 14, wherein the first member and the second member are solvent bonded using cyclohexanone or a mixture of cyclohexanone and MEK.

20. A method of bonding a first member comprising non-DEHP PVC to a second member comprising an acrylic-based polymer or an ABS-based polymer, the method comprising:

blending the acrylic-based polymer or the ABS-based polymer with an impact modifier so that a rubber content in the acrylic-based polymer or ABS-based polymer is at least 15% (w/w), wherein the impact modifier is selected from at least one of poly(butyl acrylate), poly(butyl methacrylate), methyl methacrylate-butadiene-styrene copolymer (MBS), acrylic rubber, and Elvaloy®AC;

forming the second member comprising the acrylic-based polymer or the ABS-based polymer; and solvent bonding the first member to the second member.

21. A component of a device, the component comprising:

a first member that comprises non-DEHP PVC; and a second member that comprises an acrylic-based polymer or an ABS-based polymer molded part, wherein the first member is solvent bonded to the second member, wherein the acrylic-based polymer or ABS-based polymer comprises an impact modifier so that a rubber content in the acrylic-based polymer or ABS-based polymer is greater than 12% (w/w), and wherein the impact modifier is selected from at least one of poly(butyl acrylate), poly(butyl methacrylate), methyl methacrylate-butadiene-styrene copolymer (MBS), acrylic rubber, and Elvaloy®AC.

* * * * *